US009924926B2

(12) United States Patent
Jackson et al.

(10) Patent No.: US 9,924,926 B2
(45) Date of Patent: *Mar. 27, 2018

(54) ULTRASONIC IMAGING SYSTEM WITH BODY MARKER ANNOTATIONS

(71) Applicant: KONINKLIJKE PHILIPS N.V., Eindhoven (NL)

(72) Inventors: Patty Jackson, Seattle, WA (US); Cedric Chenal, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,439

(22) Filed: Jul. 11, 2017

(65) Prior Publication Data

US 2017/0303898 A1  Oct. 26, 2017

Related U.S. Application Data

(63) Continuation of application No. 11/576,494, filed as application No. PCT/IB2005/053251 on Oct. 3, 2005, now Pat. No. 9,713,458.

(60) Provisional application No. 60/617,493, filed on Oct. 8, 2004.

(51) Int. Cl.
*A61B 8/00* (2006.01)
*A61B 8/08* (2006.01)

(52) U.S. Cl.
CPC ............ *A61B 8/465* (2013.01); *A61B 8/0825* (2013.01); *A61B 8/4405* (2013.01)

(58) Field of Classification Search
CPC ...... A61B 8/0825; A61B 8/4405; A61B 8/465
See application file for complete search history.

(56) References Cited

U.S. PATENT DOCUMENTS

| 5,709,206 | A | 1/1998 | Teboul et al. |
| 6,447,453 | B1 | 9/2002 | Roundhill et al. |
| 6,468,212 | B1 | 10/2002 | Scott et al. |
| 6,500,118 | B1 | 12/2002 | Hashimoto |
| 9,713,458 | B2 * | 7/2017 | Jackson ................. A61B 8/465 |

(Continued)

FOREIGN PATENT DOCUMENTS

| EP | 1621897 A1 | 2/2006 |
| JP | 3188837 A | 8/1991 |
| JP | 11019084 A | 1/1999 |

(Continued)

*Primary Examiner* — Ruth S Smith

(57) ABSTRACT

An ultrasonic diagnostic imaging system is operated to acquire an ultrasound image of a region of the body containing suspect anatomy such as a suspected lesion. A body marker template (104, 106) of the region of the body is displayed on a touchscreen display of the imaging system. The operator records the location of the suspect anatomy by touching a corresponding point on the body marker template displayed on the touchscreen display. The mark (120 *a*, 120 *b*) on the template can be finely adjusted by one or more controls on the imaging system control panel. The body marker template can also record a graphic indicating (120 *c*) the orientation of the ultrasound probe relative to the body when the suspect anatomy was imaged. A report generator produces a report containing both the ultrasound image of the suspect anatomy and the body marker template with the indicated location of the suspect anatomy.

16 Claims, 5 Drawing Sheets

(56) References Cited

U.S. PATENT DOCUMENTS

2002/0087061 A1  7/2002  Lifshitz et al.
2003/0212327 A1  11/2003  Wang et al.

FOREIGN PATENT DOCUMENTS

| JP | 2001143005 A | 5/2001 |
| JP | 2002263101 A | 9/2002 |
| JP | 2004267403 A | 9/2004 |
| WO | 03101303 A1 | 12/2003 |

* cited by examiner

ULTRASONIC IMAGING SYSTEM WITH BODY MARKER ANNOTATIONS

The present application is a continuation of U.S. patent application Ser. No. 11/576,494 filed Apr. 2, 2007, now U.S. No. 9,713,458 which is the U.S. National Phase application under 35 U.S.C. § 371 of International Application No. PCT/IB2005/053251, filed Oct. 3, 2005, which claims the benefit of U.S. Provisional Application Ser. No. 60/617,493 filed Oct. 8, 2004. These applications are hereby incorporated by reference herein.

This invention relates to ultrasonic diagnostic imaging systems and, in particular, to ultrasonic imaging systems in which the results of an ultrasonic diagnosis are recorded in a template corresponding to the body region being diagnosed.

Many ultrasound examinations require that the results of the exam be annotated in a way which records the location in the body of a lesion or suspicious finding. One way to do this is for the ultrasonographer to delineate the location of the abnormality on the ultrasound image graphically with labels, measurements, and icons of the pertinent anatomy. This technique is desirable when the ultrasound images are to be transferred to another clinician who is skilled in reading ultrasound images, such as a radiologist or surgeon, particularly in applications where the anatomic location is not obvious based on surrounding structures.

However, the results of an ultrasound exam frequency are forwarded to a referring physician who may not routinely read ultrasound images. In such case the diagnostic report benefits from a template which schematically represents the region of the body being diagnosed. The location of a lesion or other abnormality can be marked on the template, clearly showing the location of the abnormality to someone who is unfamiliar with the subtleties of ultrasound images. An example of a body marker graphic is given in U.S. Pat. No. 6,500,118, for instance. The selection of a body marker and use of a lesion locator tool such as this is done at the time of the exam so that the operator can clearly convey lesion or transducer location at the time of the study. This is usually done by selecting the desired template from a file of templates, then keying the annotation information of the abnormality onto the template image. This traditional technique can be overly time-consuming as the user manipulates graphics over the template with a cursor or other graphic control, at a time when it is desirable to finish the examination and the report as efficiently as possible. Accordingly it is desirable to improve the speed and accuracy with which the annotation of the examination results is performed.

In accordance with the principles of the present invention, an ultrasound system has an image display on which an ultrasound image being read is displayed, and a touchscreen display on which a body marker template is displayed. The clinician annotates the location of an abnormality by simply touching the corresponding point on the touchscreen display while observing the ultrasound image, making template annotation quick and simple. Unlike the conventional body marker user interface, the touchscreen template display can be operated by one hand. The clinician is thus not constrained to annotating only frozen images, but can enter annotations by touching the template screen with one hand while continuing to hold the ultrasound probe in contact with the patient for continuous acquisition of real time ultrasound images. In an illustrated embodiment the template annotation also enables the clinician to easily record the position of the ultrasound probe when the image of the abnormality was being acquired. Recording this information enables the abnormality to be quickly reacquired during a subsequent imaging session such as when the abnormality is being diagnosed again or treated.

IN THE DRAWINGS

Figure 5A:
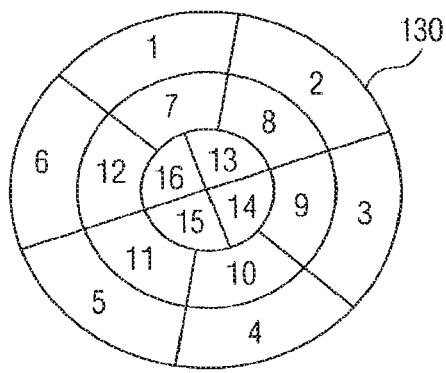

FIGS. 5 *a*-5 *c* illustrates further embodiments of cardiac body marker templates.

Figure 1:
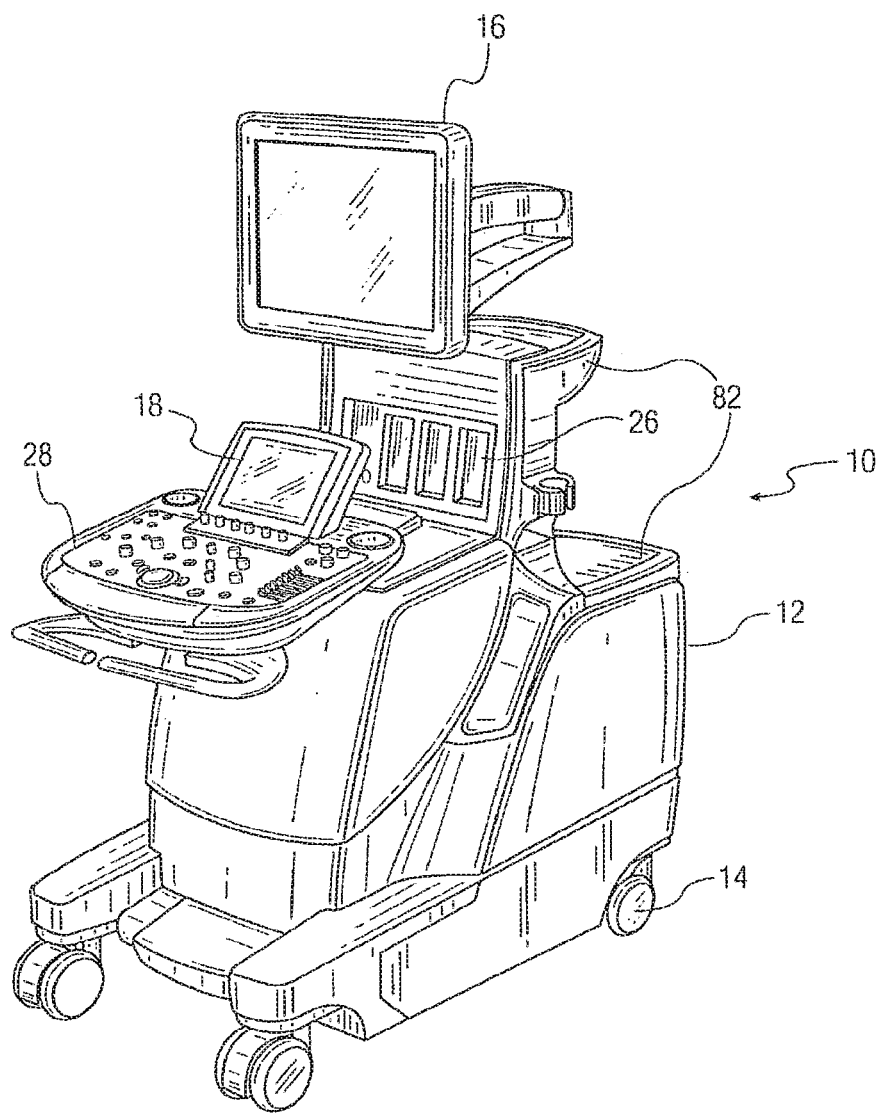
FIG. 1 illustrates in a perspective view an ultrasound system of the present invention.

Referring first to FIG. 1 an ultrasound imaging system 10 constructed in accordance with one embodiment of the invention is shown. The system 10 includes a chassis 12 containing most of the electronic circuitry for the system 10. The chassis 12 is mounted on a cart 14, and an ultrasound image display 16 is mounted on the chassis 12. Different imaging probes may be plugged into three connectors 26 on the chassis. The chassis 12 includes a keyboard and controls, generally indicated by reference numeral 28, for allowing a sonographer to operate the ultrasound system 10 and enter information about the patient or the type of examination that is being conducted. At the back of the control panel 28 is a touchscreen display 18 on which body marker templates are displayed in accordance with the present invention. The sonographer enters information on the touchscreen display 18 simply by touching a point on the display screen.

In operation, a probe which is plugged into one of the connectors 26 is placed against the skin of a patient (not shown) and a particular anatomy of the patient such as the breast or heart is imaged on the image display 16. The images may be examined as they are acquired in real time, or selected images may be frozen and stored. A body marker template corresponding to the anatomy being examined is accessed and displayed on the touchscreen display 18, either at the start of the examination or when particular pathology is diagnosed in one of the images on the display. The ultrasonographer with then mark the location of the pathology on the template by simply touching the appropriate location on the template and/or making further refinements as discussed more fully below. The template can then be incorporated into the diagnostic report along with one or more of the images showing the abnormality as discussed below.

Figure 2:
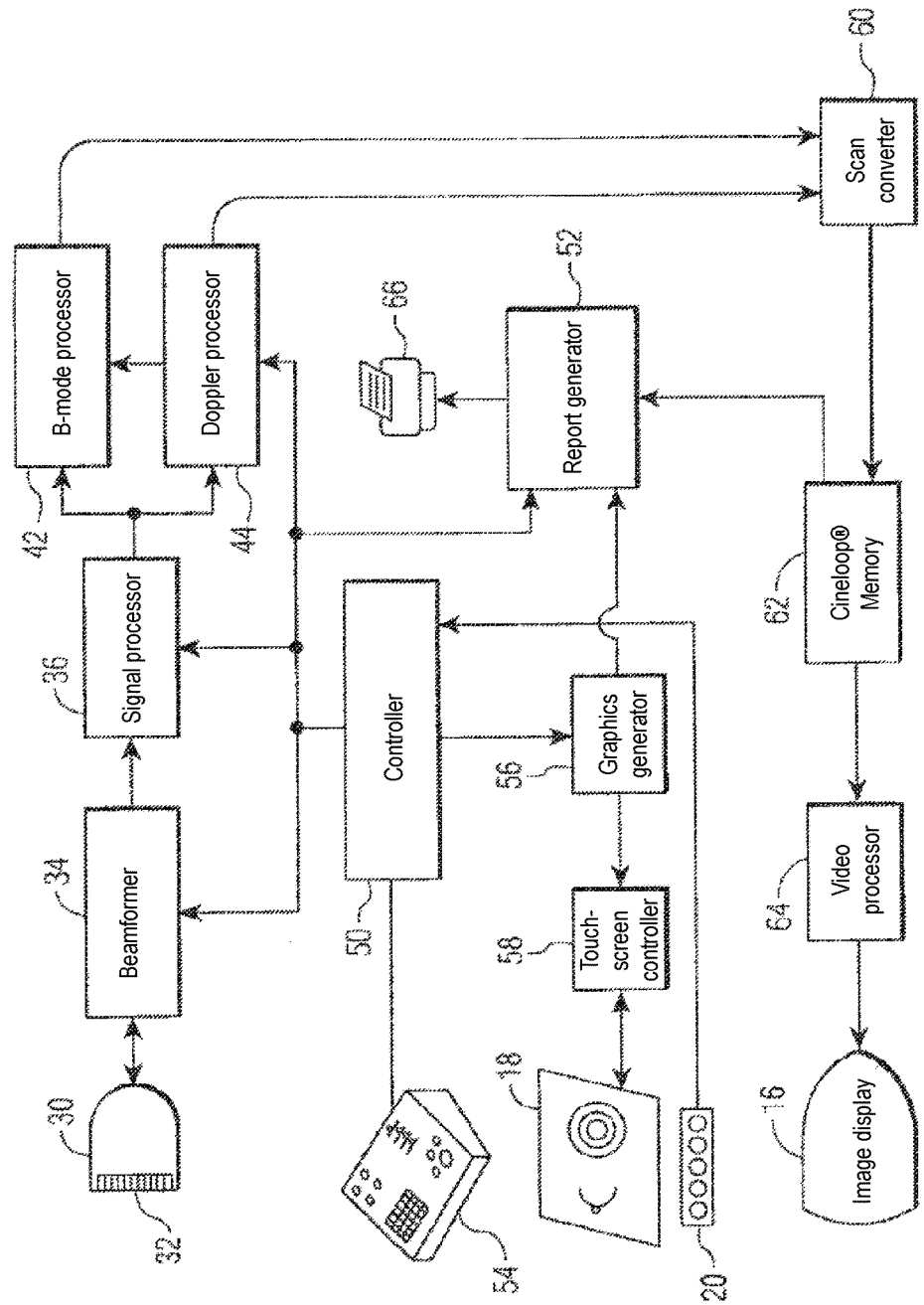
FIG. 2 illustrates in block diagram form an embodiment of an ultrasonic diagnostic imaging system constructed in accordance with the principles of the present invention.

A block diagram of an ultrasound system constructed in accordance with the principles of the present invention is shown in FIG. 2. A probe 30 has a multi-element array transducer 32 which transmits ultrasound waves into a subject and receives echo signals. The echo signals are converted into electrical signals by the transducer elements and coupled to a beamformer 34. Preferably the transducer signals are digitized and the processed digitally in the beamformer. The beamformer forms coherent echo signals when then undergo processing by a signal processor 36 such as quadrature detection, wall filtering (for Doppler signals), or other filtering for signal enhancement such as harmonic signal separation or spatial or frequency compounding. The processed signals are then coupled to a B mode processor 42 for B mode imaging which involves the envelope detection of signals from tissue structure, or are processed by a Doppler processor 44 to produce images of the motion of blood flow or moving tissue. The coordination of the beamformer 34, the signal processor 36, the B mode and Doppler processor 44, as well as the other processing steps in the ultrasound signal path prior to display such as scan conversion, is performed by a controller 50. The resultant 2D or 3D tissue, motion or spectral Doppler image signals are arranged in the desired display format by a scan converter 60. The ultrasound images are then coupled to a Cineloop® memory 62 where an entire sequence of real time images may be captured and replayed for diagnosis. Individual images or a loop (sequence) of images may be stored in an image store (not shown) for later further diagnosis. The images in the Cineloop memory are applied to a video processor 64 which drives the image display 16 in the appropriate manner for display of the images.

The ultrasound system is operated by a user who manipulates the appropriate controls of a control panel 54. Signals from the control panel are received by the controller 50 which responds by controlled the ultrasound system as desired by the operator. In accordance with the present invention, the user can use the control panel to call up a body marker template for display on the touchscreen display 18. Alternately, the ultrasound system may call up a particular template in correspondence with selection by the user of a particular ultrasound exam. For instance, if the user indicates that a breast exam will be performed, the ultrasound system may call up the templates for a breast diagnosis. The graphical templates are applied to a graphics generator 56, which applies the graphics signals to a touchscreen controller 58, which drives the touchscreen display appropriately to display the selected template. Located below the touchscreen display as seen in FIG. 1 is a row of control knobs 20 which are coupled to the controller so that signals from the control knobs can be received by the controller and the appropriate responses made as described below. A report generator 52 is also resident on the ultrasound system and assists in the assembly of a diagnostic report for the examination. The report generator 52 is also controlled by the controller 50. The report generator can access ultrasound images from the Cineloop memory 62 and body marker templates from the graphics generator 56 for assembly into a diagnostic report. The diagnostic report can be viewed on one of the display screens and/or printed on a printer 66.

Figure 3:
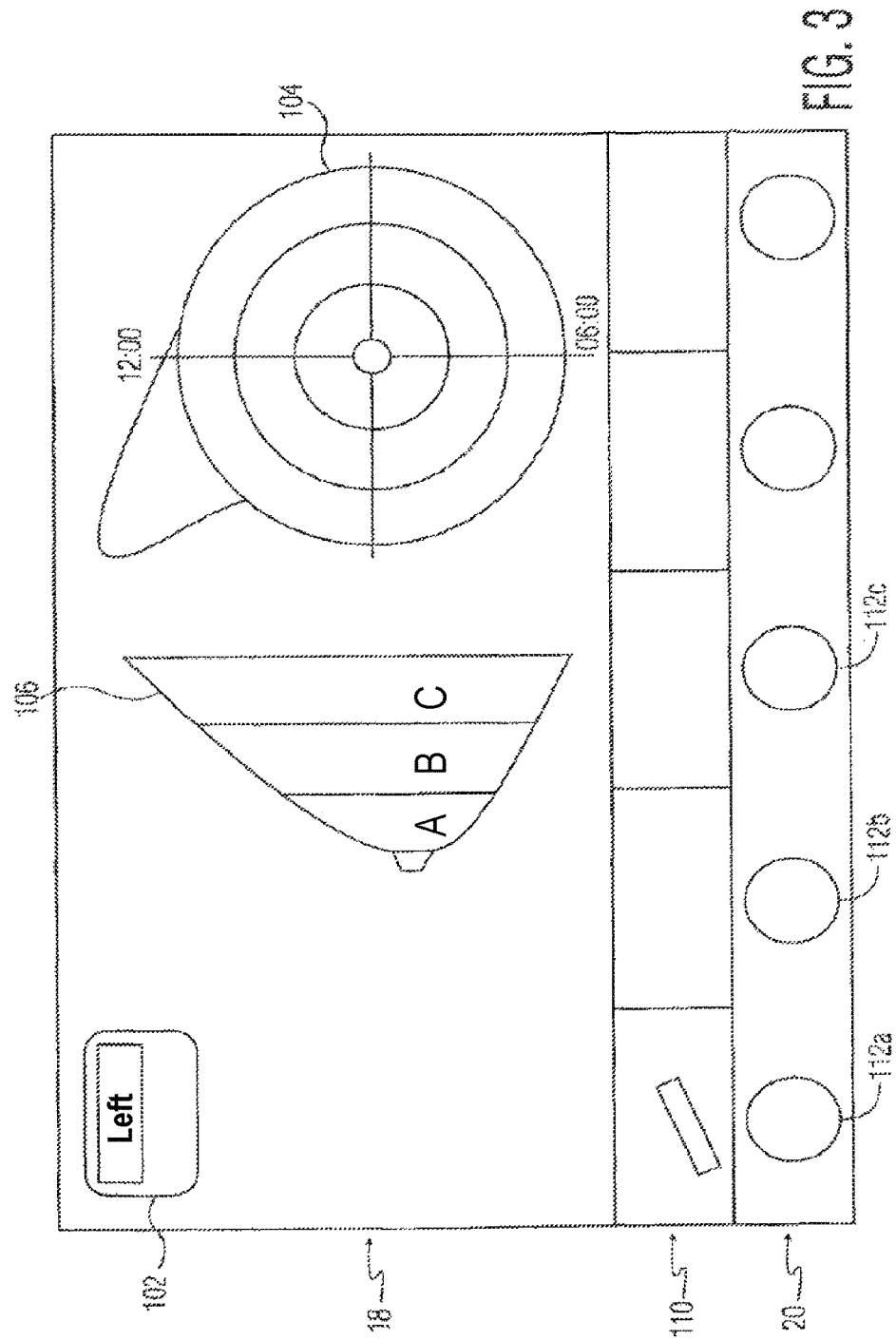
FIG. 3 illustrates a first embodiment of a touchscreen with a breast body marker template displayed.

FIG. 3 shows a breast exam embodiment of the present invention as it appears on the touchscreen 18. A graphic 102 in the upper left corner of the touchscreen display indicates whether the displayed breast template is for the left or right breast. The user can change between left and right breast templates with a single control on the touch screen. In this example the template is for the left breast and the word "Left" is highlighted. If the template is to be used for diagnosis of the right breast, the word "Right" would be touched by the user, causing this graphic on the template to be highlighted. In the center of the touchscreen display is a side view template and on the right side of the screen is a front view template of the breast. These two templates enable the three dimensional location of an abnormality to be clearly marked. The side view template is segmented into A, B and C depth zones to mark the depth of an abnormality and the radial zones of the front view template indicate the angular orientation and radial distance of an abnormality relative to the nipple in the center.

Located in a row 110 at the bottom of the touchscreen display 18 are five softkeys. These softkeys are operated by the control knobs 20 located below the respective softkeys. In this embodiment only the first three softkeys are used and are controlled by knobs 112 *a*, 112 *b*, and 112 *c*.

Figure 4:
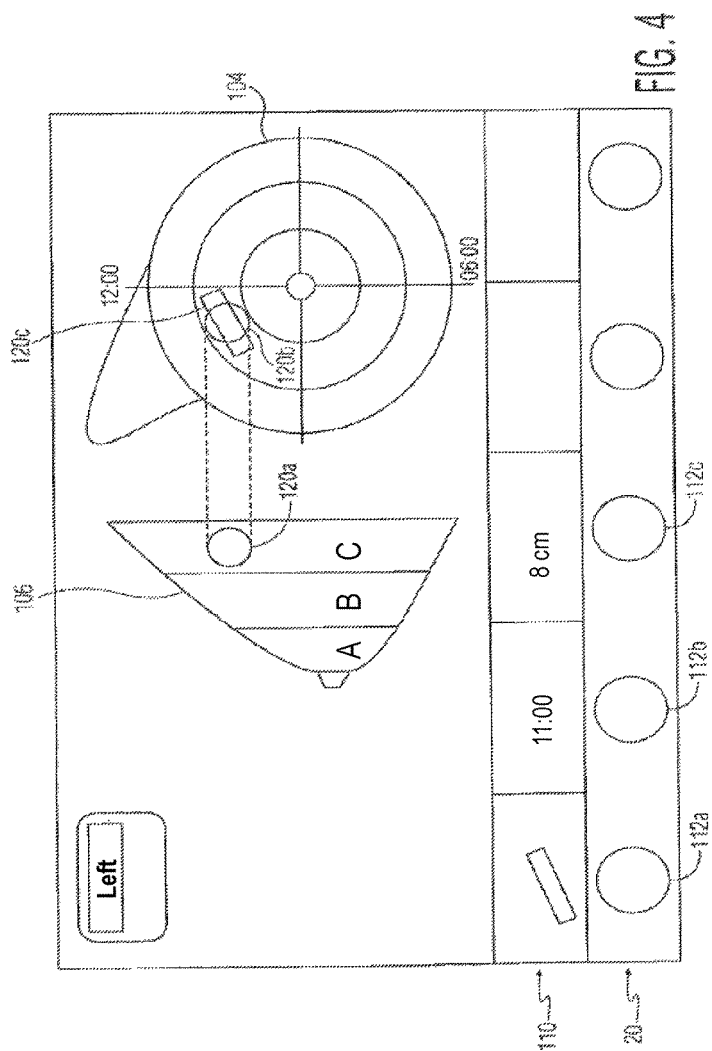
FIG. 4 illustrates the body marker template of FIG. 3 after annotation.

When the user finds an abnormality in a breast image on the image display 16, the location of the abnormality in the breast is annotated on the breast template as shown in FIG. 4. In this example the sonographer has found an abnormality in the deepest region C of the left breast and at the 11 o'clock position radially relative to the center nipple. The abnormality is in the second radial segment out from the nipple. The sonographer indicates this position by touching the appropriate location on either the side or front template, which causes the ultrasound system to respond by displaying a circle 120 *a*, 120 *b* on the touchscreen display. In the illustrated embodiment two markers 120 *a*, and 120 *b* are used. Each of the markers may be placed by manually touching the screen. Alternatively, when one of the templates 104, 106 is touched, a corresponding marker is automatically placed on the other template 106, 104. The position of the second marker is then precisely adjusted. This may be done by manually touching a marker and then dragging it with the finger into the proper location on the touchscreen. However in the illustrated embodiment the position of the marker 120 *b* can be finely adjusted with the control knobs 112 *b* and 112 *c*. Turning the knob 112 *b* will cause the marker 120 *b* to rotate around the nipple position. In the illustrated embodiment the marker 120 *b* has been adjusted to the 11 o'clock position and "11:00" appears in the softkey graphic above knob 112 *b*. The marker 120 *b* can be moved radially outward and inward from the nipple position in the front template 104 by turning the control knob 112 *c*. As this adjustment is made the current position of the marker is indicated on the softkey graphic. In this example 8 cm is shown on the softkey. As the marker 120 *b* is moved on the front template 104 the marker 120 *a* will move correspondingly on the side template 106. In this embodiment two dashed lines join the markers in the two templates to indicate their correspondence. It will be appreciated that another softkey and knob can be used to adjust the position of the marker 120 *a* in the side template, enabling the user to precisely adjust the indicated depth of the abnormality in the side template 106.

This embodiment also enables the sonographer to indicate the position of the probe when the ultrasound image shown on the image display 16 was acquired. This information will enable the abnormality to be imaged in the same way in a subsequent exam or treatment procedure. The front template 104 is seen to have a rectangular graphic 120 *c* positioned over the abnormality marker 120 *b*. This rectangular graphic corresponds to the rectangular shape of the transducer array 32 of the probe. In this embodiment the rectangular probe graphic 120 *c* automatically appears over the abnormality marker 120 *b*. The probe graphic must then be adjusted by the sonographer which is done by turning softkey knob 112 *a*. This causes the rectangular graphic to rotate about its center until it is in the same position that the sonographer was holding the probe when the image being annotated was acquired. Similar to the other softkeys, the probe orientation softkey has a rectangular graphic which rotates in the same manner as the probe graphic 120 *c*. With the probe graphic properly positioned the abnormality can be imaged in the same manner as shown in the currently display image at a later date.

FIGS. 5 *a*-5 *c* illustrate exemplary body marker templates for another embodiment of the present invention, a cardiac exam. When the myocardium is being examined for indicia of infarction by wall motion abnormalities, the location of a wall defect is conventionally marked on a template such as a bullseye scorecard 130 as shown in FIG. 5 *a*. The bullseye scorecard 130 represents areas of the myocardium distributed around the apex of the heart which is represented by the center of the scorecard. When the echocardiographer discerns an abnormality in wall motion the location where the abnormality was found is located on the scorecard. The scorecard 130 is displayed on the touchscreen display and the clinician simply touches the appropriate segment of the scorecard to mark the location of the abnormality. In one embodiment the segment touched by the clinician can simply darken or brighten on the display. If a color display is used the touch of the user can mark a color on the scorecard. For example, touching a segment once can cause the segment to turn yellow, indicating a heart wall location where the wall motion is suspect. Touching the segment twice in rapid succession can cause the segment to turn red, indicating a location where wall motion is definitively abnormal. Touching a colored segment again will eliminate the color, thereby enabling the clinician to correct an incorrectly marked segment.

Figure 5B:
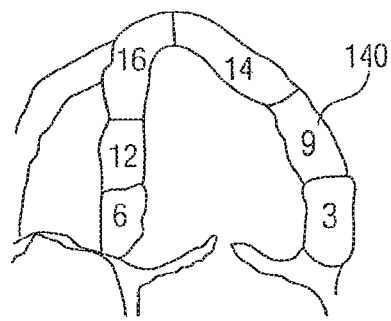
Figure 5C:
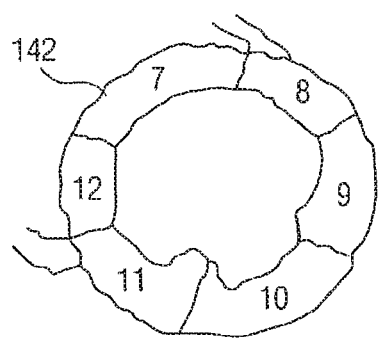

FIGS. 5*b* and 5*c* illustrate cardiac templates for an exam where four-chamber and transverse views of the heart are acquired. As explained in U.S. Pat. No. 6,447,453, these template have high anatomical accuracy as they are created from automatically drawn and segmented boundary tracings of the inside and outside of the myocardium, the endocardium and the epicardium. The four-chamber template 140 and the transverse template 142 thus closely correspond to the anatomy as seen in the image being diagnosed. As in the previous example, the appropriate segment or segments of the templates are touched by the user to indicate a suspicious region of the heart wall where abnormal wall motion was detected. Precise body marker templates are thus formed quickly and marked rapidly, improving the efficiency of the diagnostic exam. At the completion of the exam a report is produced which contains both the ultrasound image(s) being diagnosed and the corresponding templates, clearly indicating to the referring physician the location of an abnormality.

While the templates may be indexed in a file system on the ultrasound system and called up by the user addressing the appropriate body marker template, it is sometimes desirable to have the templates called up and displayed automatically. This may be done when the user is carrying out a diagnostic protocol, a series of exam steps, which has been pre-programmed on the ultrasound system. In such case the selection of each step of the protocol by the user would automatically call up and display the appropriate body marker template for the imaging procedure of that step. This obviates the need to manually search for and call up the template for each imaging procedure of the protocol. Transition from one marker template to another (including left/right and annotations) is driven by the protocol, which are then modified by the user through the easy touchscreen interface.

What is claimed is:

1. An ultrasonic diagnostic imaging system, comprising:
a probe for acquiring ultrasonic echo signals;
an image processor coupled to the probe;
an image display configured to display an ultrasonic image produced from the acquired ultrasonic echo signals;
a storage medium comprising a stored body marker template comprising a graphical representation of anatomy; and
a touchscreen display that is coupled to the storage medium and configured to display the stored body marker template, wherein the touchscreen display is responsive to a manual touch of an imaging system operator and configured to indicate on the body marker template a location of a region of the anatomy identified in the ultrasonic image.

2. The ultrasonic diagnostic imaging system of claim 1, wherein the graphical representation of anatomy comprises at least a portion of a breast.

3. The ultrasonic diagnostic imaging system of claim 1, wherein the graphical representation of anatomy comprises at least a portion of a heart.

4. The ultrasonic diagnostic imaging system of claim 1, wherein the touchscreen display is further responsive to the manual touch of the imaging system operator to reposition an indication on the body marker template of the region of the anatomy.

5. The ultrasonic diagnostic imaging system of claim 1, further comprising a body marker user control configured to adjust a position of the location of the region of the anatomy identified in the ultrasonic image.

6. The ultrasonic diagnostic imaging system of claim 5, wherein the anatomy comprises a breast, and the touchscreen display is responsive to the body marker user control to adjust an indicated depth in the breast.

7. The ultrasonic diagnostic imaging system of claim 5, wherein the anatomy comprises a breast, and the touchscreen display is responsive to the body marker user control to adjust an radial position associated with the breast.

8. The ultrasonic diagnostic imaging system of claim 1, wherein the image display and the touchscreen display are different displays.

9. The ultrasonic diagnostic imaging system of claim 1, further comprising a diagnostic report generator that is configured to generate a diagnostic report containing the ultrasonic image and the body marker template.

10. A method of recording the location of suspect anatomy identified in an ultrasound image, the method comprising:
displaying an ultrasound image containing suspect anatomy;
displaying a body marker template representing a portion of the body containing the anatomy on a touchscreen display of an ultrasonic imaging system; and
in response to a manual touch of an imaging system operator, marking a location of the suspect anatomy on the body marker template.

11. The method of claim 10, wherein the ultrasound image comprises breast tissue, and the body marker template represents at least a portion of a breast.

12. The method of claim 10, wherein the ultrasound image comprises heart tissue, and the body marker template represents at least a portion of a heart.

13. The method of claim 10, comprising adjusting a position of the location on the displayed body marker template previously marked in response to the manual touch.

14. The method of claim 10, comprising displaying a graphic of a position of a probe used to acquire the ultrasound image containing suspect anatomy.

15. The method of claim 10, comprising producing a report containing the ultrasound image containing suspect anatomy and the body marker template.

16. The method of claim 10, comprising executing an exam protocol stored on an ultrasound system, wherein the body marker template is selected through the operation of the exam protocol.

* * * * *